United States Patent

Wong

Patent Number: 6,146,331
Date of Patent: Nov. 14, 2000

[54] METHOD FOR IMPROVED CLUTTER SUPPRESSION FOR ULTRASONIC COLOR DOPPLER IMAGING

[75] Inventor: Tommy Wong, Issaquah, Wash.

[73] Assignee: Siemens Medical Systems, Inc., Iselin, N.J.

[21] Appl. No.: 09/164,386

[22] Filed: Sep. 30, 1998

[51] Int. Cl.$^7$ .................................... A61B 8/00
[52] U.S. Cl. ............................................. 600/454
[58] Field of Search ................................ 600/454–456

[56] References Cited

U.S. PATENT DOCUMENTS

| | | | |
|---|---|---|---|
| 4,683,893 | 8/1987 | Mayo | 128/660 |
| 4,850,364 | 7/1989 | Leavitt | 128/661.09 |
| 4,896,674 | 1/1990 | Seo | 128/661.09 |
| 5,243,987 | 9/1993 | Shiba | 128/660.06 |
| 5,341,808 | 8/1994 | Rickey et al. | 128/660.01 |
| 5,349,525 | 9/1994 | Dunki-Jacobs et al. | 364/413.25 |
| 5,494,037 | 2/1996 | Banjanin et al. | 600/455 |
| 5,522,393 | 6/1996 | Phillips et al. | 600/455 |
| 5,553,621 | 9/1996 | Otterson | 600/455 |
| 5,653,234 | 8/1997 | Kim et al. | 128/660.01 |
| 5,664,571 | 9/1997 | Yamazaki | 600/455 |
| 5,706,817 | 1/1998 | Song et al. | 128/661.09 |
| 5,706,819 | 1/1998 | Hwang et al. | 128/662.02 |
| 5,709,209 | 1/1998 | Friemel et al. | 128/660.07 |
| 5,709,210 | 1/1998 | Green et al. | 128/661.07 |
| 5,740,806 | 4/1998 | Miller | 128/661.01 |
| 5,913,824 | 6/1999 | Ogasawara et al. | 600/455 |

OTHER PUBLICATIONS

"Bias and Variance in the Estimate of the Doppler Frequency Induced by a Wall Motion Filter," J. C. Willemetz, et al., taken from Ultrasonic Imaging, vol. 11, pp. 215–225 (1989).

"On the Performance of Regression and Step–Initialized IIR Clutter Filters for Color Doppler Systems in Diagnostic Medical Ultrasound," by Anthony P. Kadi & Thanasis Loupas, IEEE Transactions on Ultrasonics, Ferroelectrics and Frequency Control, vol. 42, No. 5, Sep. 1995, pp. 927–937.

*Primary Examiner*—Francis J. Jaworski

[57] ABSTRACT

A Doppler ultrasound clutter suppression system and method in which the clutter is first low-pass filtered (716) to suppress the flow component (4024) just before mean frequency estimation (718). The mean frequency is then estimated and mixed with the original clutter data which is positioned at DC. The low-pass filter bandwidth is predetermined based on the particular application and imaging parameters. The signal is then high-pass filtered (726) to remove the clutter component (4022).

14 Claims, 6 Drawing Sheets

METHOD FOR IMPROVED CLUTTER SUPPRESSION FOR ULTRASONIC COLOR DOPPLER IMAGING

BACKGROUND OF THE INVENTION

1. Field of the Invention

The present invention relates to an ultrasonic imaging system, and more particularly, to a filtering method for removing a low-frequency Doppler signal from an ultrasound image.

2. Description of the Related Art

Medical imaging systems are used as diagnostic tools for viewing internal areas of the patient's body. Imaging systems based on ultrasound technology are desirable because such systems are non-invasive, portable and generally easy to use. A Doppler ultrasound system displays a frequency deviation amount together with a scattering strength of the signal as image on a screen to enable evaluation of a dynamic function of a living body. In particular, the Doppler imaging system is capable of displaying color images and demodulates a received signal and digitizes the demodulated signal, thereby imaging a flow of blood flowing through a heart or blood vessel into a real-time two-dimensional image. Such color Doppler imaging systems can display cross-sectional images and blood flow information simultaneously. To discriminate the layer image and the blood flow information, the cross-sectional image is indicated as white and black and the blood flow information is indicated as color.

Although an ultrasound beam is focused, some part of the Doppler sample volume typically lies outside the blood vessel. This results in the ultrasound instrument receiving a signal from the vessel wall and surrounding tissue (referred to as the clutter component), as well as from the blood flowing in the vessel (referred to as the flow component). The clutter component returned from the wall and tissue has an amplitude that is generally many times greater than the flow component. Because of respiration and cardiac motion, the tissue and vessel tend to move at slower velocities than the flowing blood. The Doppler signal also contains noise produced by the Doppler instrument's electronics. As such, the Doppler signal is a composite signal composed of a clutter component, a flow component and a noise component. The flow component tends to have a low amplitude and high-frequency, while the clutter component tends to have a large amplitude and low-frequency. In order to ensure clinical efficiency, Doppler instruments must be able to determine the velocity of moving blood accurately in the presence of clutter and noise signal components. Accordingly, the clutter component is generally removed from the composite Doppler signal via filtering prior to velocity estimation. If the clutter component is not filtered, the velocity measurement returns to the velocity of the moving tissue and not of the moving blood. Typically, a high-pass filter referred to as a wall filter is used to remove the clutter component of the signal while leaving the flow component intact.

For example, conventional clutter processing uses a mean frequency method to estimate the clutter frequency. The clutter frequency is then mixed with the original clutter data in an attempt to position the clutter at a predetermined DC level. The conventional method assumes that flow has little effect on the mean frequency estimation. However, this assumption is not valid when the flow component is comparable to the clutter component in amplitude which may occur, for example, in the middle of a big vessel where the effect of clutter is much smaller than at the vessel boundary and/or where contrast agents are used to boost flow amplitude. This may cause the mean frequency clutter frequency to shift towards the blood flow frequency. When flow velocity is high, the mean frequency shifts toward the flow frequency even more. When this frequency is mixed with the clutter, a combination of the following results: (1) clutter is not positioned at the predetermined DC level resulting in incomplete clutter cancellation; (2) clutter may be even further from the predetermined DC level than it would have been without mixing; and (3) strong blood flow can be misinterpreted as clutter and thus shifted erroneously close to the predetermined DC level, resulting in either incorrect velocity estimation or cancellation by a subsequent wall filter. Conventionally, a combination of clutter mean frequency, power and variance may be used in an attempt to identify such situations and disable mixing accordingly. Although this may mitigate the effect of the strong blood flow being misinterpreted as clutter, clutter residue may still be excessive due to the inaccurate positioning of the clutter away from the predetermined DC level.

Accordingly, there is a need for an improved method for eliminating clutter components from Doppler ultrasound signals. There is a further need for a method for removing clutter components from Doppler ultrasound signals when the flow component is comparable in amplitude to the clutter component. There is further a need to remove the clutter component from the flow component when flow velocity is relatively high.

SUMMARY OF THE INVENTION

These problems in the prior art are overcome in large part by a Doppler ultrasound clutter suppression system and method according to the present invention. In particular, in the present invention the clutter is first low-pass filtered to suppress the flow component just before mean frequency estimation. The mean frequency is then estimated and mixed with the original clutter data and positioned at a predetermined DC level. The low-pass filter bandwidth is predetermined based on the particular application and imaging parameters. When the imaging parameters are altered, the filter bandwidth similarly is altered to compensate for the change in clutter bandwidth.

According to one embodiment, the low-pass filter is a regression-type digital filter. It is noted, however, that other types of filters, such as IIR or FIR filters are contemplated. Moreover, the low-pass filter may be embodied as an analog filter.

BRIEF DESCRIPTION OF THE DRAWINGS

A better understanding of the present invention is obtained when the following detailed description is considered in conjunction with the following drawings in which.

DETAILED DESCRIPTION OF THE INVENTION

Figure 5:
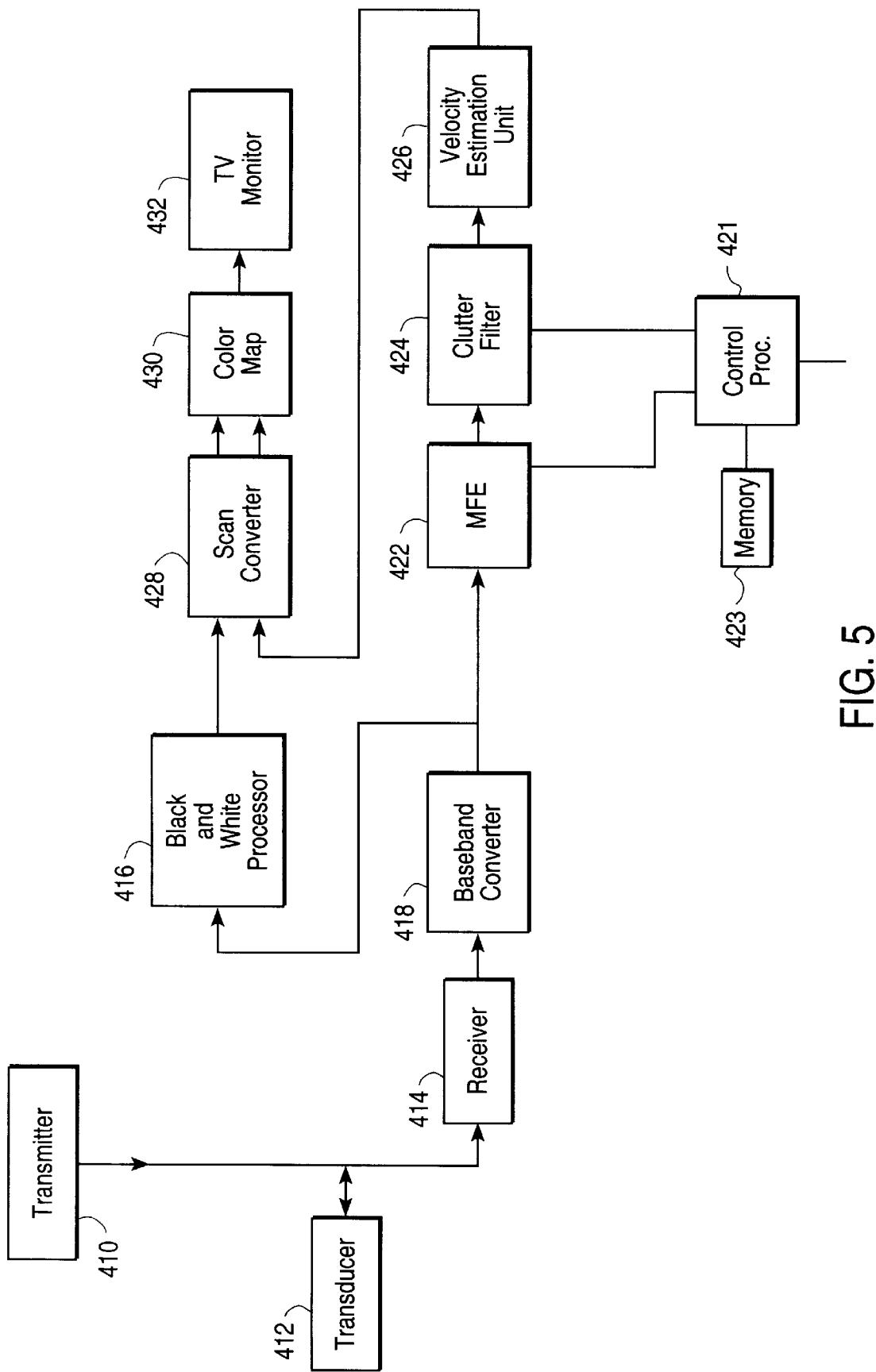
FIG. 5 illustrates an exemplary ultrasound system employing clutter suppression.

Turning now to the drawings, and with particular attention to FIG. 5, a block diagram of an exemplary ultrasound imaging system is shown. An ultrasound transmitter 410 transmits ultrasound energy through an ultrasound transducer 412, which typically includes an array of ultrasound transducer elements. The ultrasound energy is transmitted into a target region of a patient. A portion of the transmitted ultrasound energy is reflected by various components of the target region. Reflected ultrasound energy is received by the transducer 412 and is input to a receiver 414, which performs an analog-to-digital conversion and focuses the signals from the multiple transducer elements.

The signals from the receiver 414 are input to a black and white processor 416 and to a base band converter 418. The base band converter 418 converts the RF frequencies to base band and inputs the base band signals to the black and white processor 416 and to a mean frequency estimator 422. The mean frequency estimator 422 may include further frequency shifting to position the clutter signal components at DC and low-pass filtering according to the present invention. A control processor 421 coupled to a memory 423 may be provided to receive user inputs and adjust bandwidths of the low-pass filter and the wall filter, as will be discussed in greater detail below. The samples output from the mean frequency estimator 422 are provided to a wall filter 424. As noted previously, in color Doppler imaging systems, stationary and slowly moving targets produce large, low frequency signals. These unwanted signals, positioned accurately at DC by the mean frequency estimator 422 according to the present invention, are removed by the wall filter 424 to detect the higher frequency Doppler blood echoes. Outputs of the wall filter 424 are input to a velocity estimation unit 426 which makes an estimate of the velocity of blood in the target region.

The velocity estimate and the output of the black and white processor 416 are input to a scan converter 428 which converts the color and black and white data from acoustic space to raster space coordinates. A color map unit 430 maps black and white data and velocities output by the scan converter 428 to color and brightness, which are displayed on a TV monitor 432. An exemplary ultrasound system including a wall filter 424, a black and white processor 416, a scan converter 428, and a color map unit 430 is the Elegra, available from Siemens Medical Systems, Inc.

It is noted that, while the analog to digital conversion is illustrated as occurring before base band conversion and the mean frequency estimation, the analog to digital conversion may equally be performed after it, and in fact, may be performed after wall filtering. Thus, FIG. 5 is exemplary only.

Figure 1:
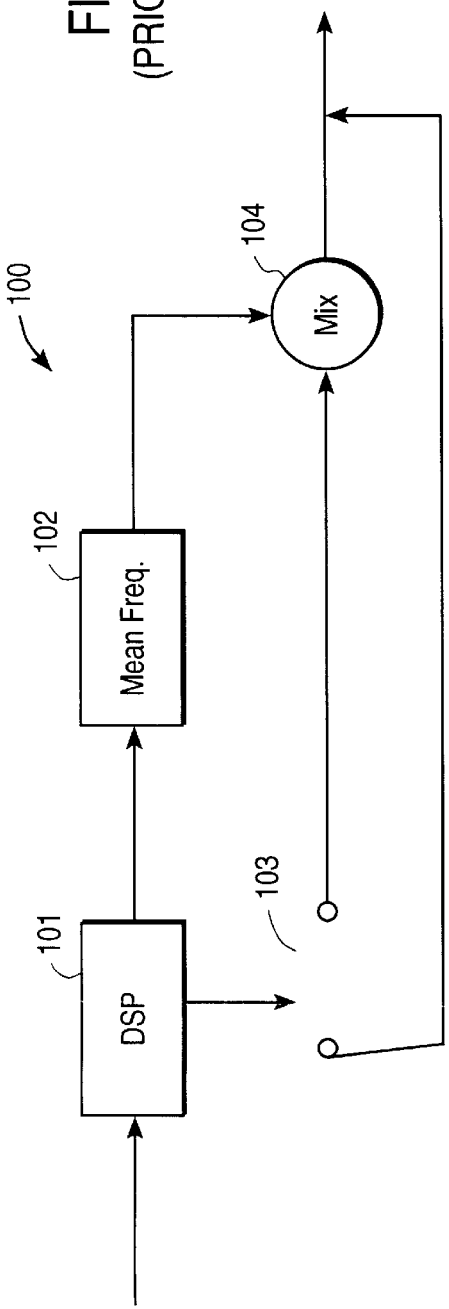
FIG. 1 is a diagram illustrating an exemplary clutter suppression system according to the prior art.

A block diagram showing an exemplary clutter suppression mechanism or mean frequency estimation block 420 according to the prior art is shown in FIG. 1. In particular, the mean frequency estimator 100, may correspond generally to the mean frequency estimator 420 of FIG. 5, and includes a frequency estimator 102, which receives the received base band Doppler signal. The received base band Doppler signal is also provided to a mixer 104. The output of the frequency estimator 102 is mixed with the received base band Doppler signal input. The output of the mixer 104 is assumed to position the clutter signal at DC. As discussed above, the mean frequency estimator 100 may further include one or more digital signal processors (DSP) 101 for computing clutter mean velocity, power and variance to disable mixing under certain circumstances, discussed above. This is represented schematically by a switch 103. It is noted that the mean frequency estimation and the DSP functions described above are typically accomplished using the same DSP; thus, the FIG. 1 is exemplary only. If is further noted that the DSP operations may occur in parallel with the mean frequency estimation. The mixed signal (or the bypass signal) is then provided to a wall filter such as the wall filter 424 of FIG. 5. The wall filter 424 is typically a high-pass filter to eliminate the low frequency clutter components. However, as discussed above, this system is disadvantageous in that it cannot account for the case in which the flow signal is of similar magnitude to the clutter signal.

Figure 2:
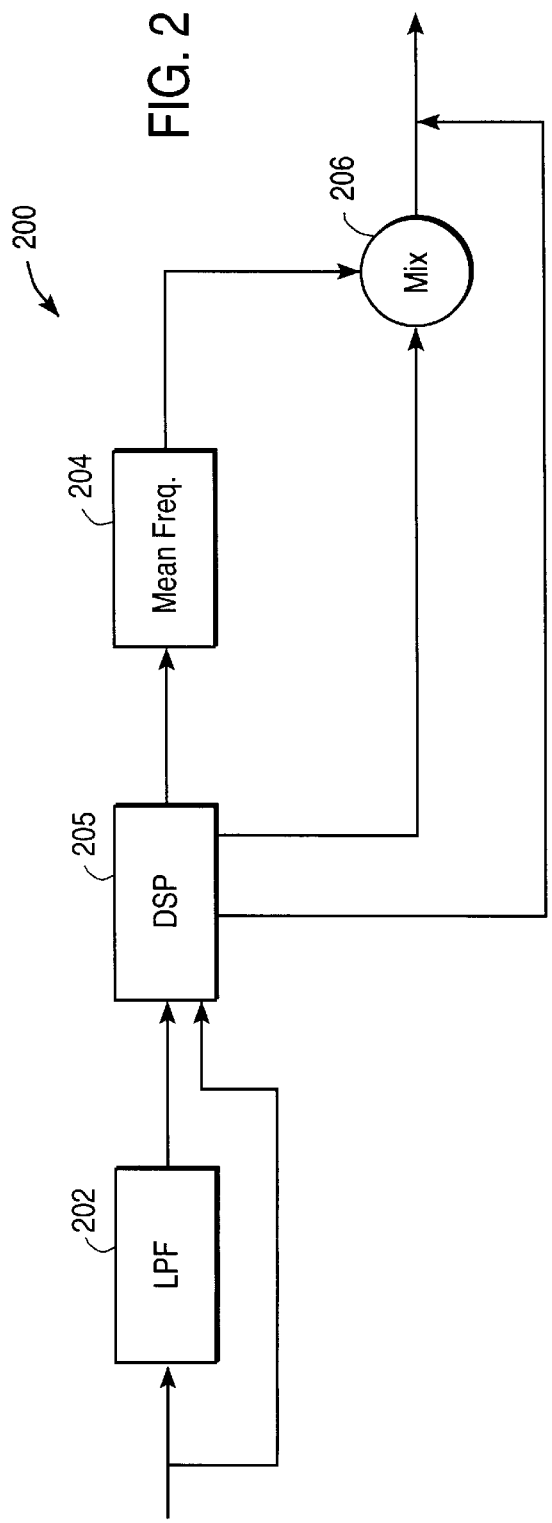
FIG. 2 is a diagram illustrating an exemplary clutter suppression system according to an embodiment of the present invention.

Accordingly, with reference to FIG. 2, an improved clutter suppression system or mean frequency estimation block 200, according to the present invention, is illustrated. Again, the mean frequency estimation block 200 corresponds generally to the mean frequency estimator 420 of FIG. 5. In this case, however, the received base band Doppler signal is input to a low-pass filter 202. The low-pass filter 202 may be any low-pass filter adequate to filter the flow component of the color Doppler signal. In particular, the low-pass filter 202 may be a digital regression-type filter of the type described in Kadi, et al., "On the Performance of Regression and Step-Initialized IIR Clutter Filters for Color Doppler Systems in Diagnostic Medical Ultrasound," IEEE Transactions on Ultrasonics, Ferroelectrics, and Frequency Control, Vol. 42, No. 5, Sep. 1995, which is hereby incorporated by reference in its entirety as if fully set forth herein. It is noted, however, that other types of low-pass filters may be employed.

The output of the low-pass filter 202 is provided to a DSP or other processing or control unit 205, as will be described below. The DSP 205 may cause the signal to be provided to a frequency estimator 204, and then may also be provided to a mixer 206. The output of the frequency estimator 202 is mixed with the received Doppler signal input. The mixed signal is then provided to a wall filter such as the wall filter 424 of FIG. 5. The wall filter 106 is typically a high-pass filter to eliminate the low frequency clutter components. Alternatively, the DSP 205 may cause the received base band signal to be provided directly to the wall filter.

As in the example shown in FIG. 1, the DSP 205 may be provided to receive the low pass filter output for mean velocity, power and variance calculations. If one or more predetermined conditions are met, no mixing and mean frequency of estimation may occur. For example, if the power level is less than a predetermined threshold, no shifting will occur. This may be the case, for example, where there is a flow component, but no clutter component. In that case, the clutter power is compared to the noise level. If the clutter power is below noise, then no mixing is permitted.

Figure 3:
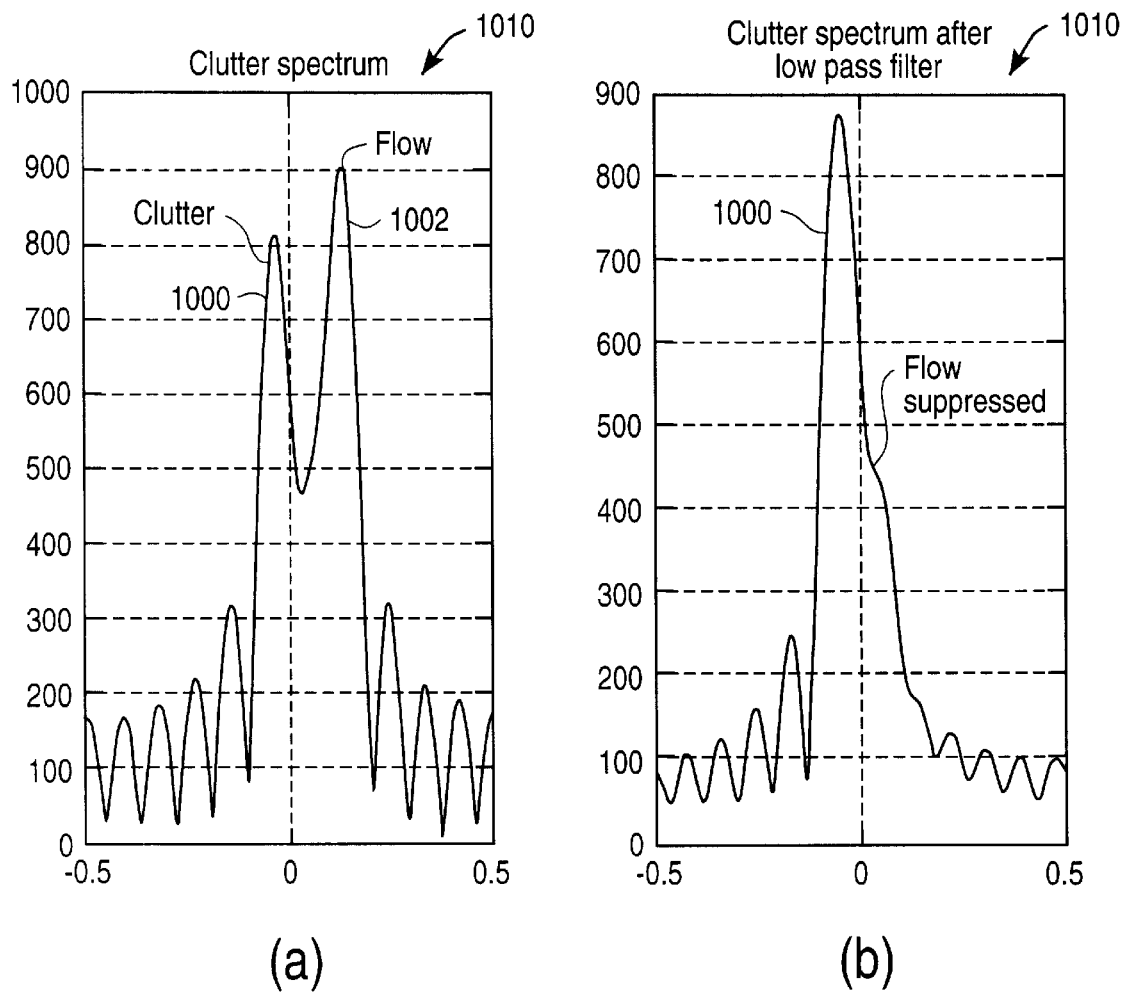
FIG. 3A and FIG. 3B are an exemplary color spectrum before and after being low-pass filtered.

An exemplary response characteristic for the low-pass filter 202 is shown in FIG. 3A and 3B. In particular, FIG. 3A illustrates a color spectrum 1010 sampled close to the center of a carotid artery. As can be seen, the color spectrum includes a clutter peak 1000 and a flow peak 1002. In the example shown, the flow peak 1002 is actually higher in magnitude than the clutter peak 1000.

FIG. 3B illustrates the color spectrum 1010 after low-pass filtering has occurred. As can be seen, the clutter peak 1000 is still prominent, but the flow peak 1002 has been almost completely eliminated. The low-pass filter 102 thus compensates for the prominent flow peak 1002. The output of the low-pass filter 102 is then provided to the mean frequency estimator 204, as discussed above.

Figure 4:
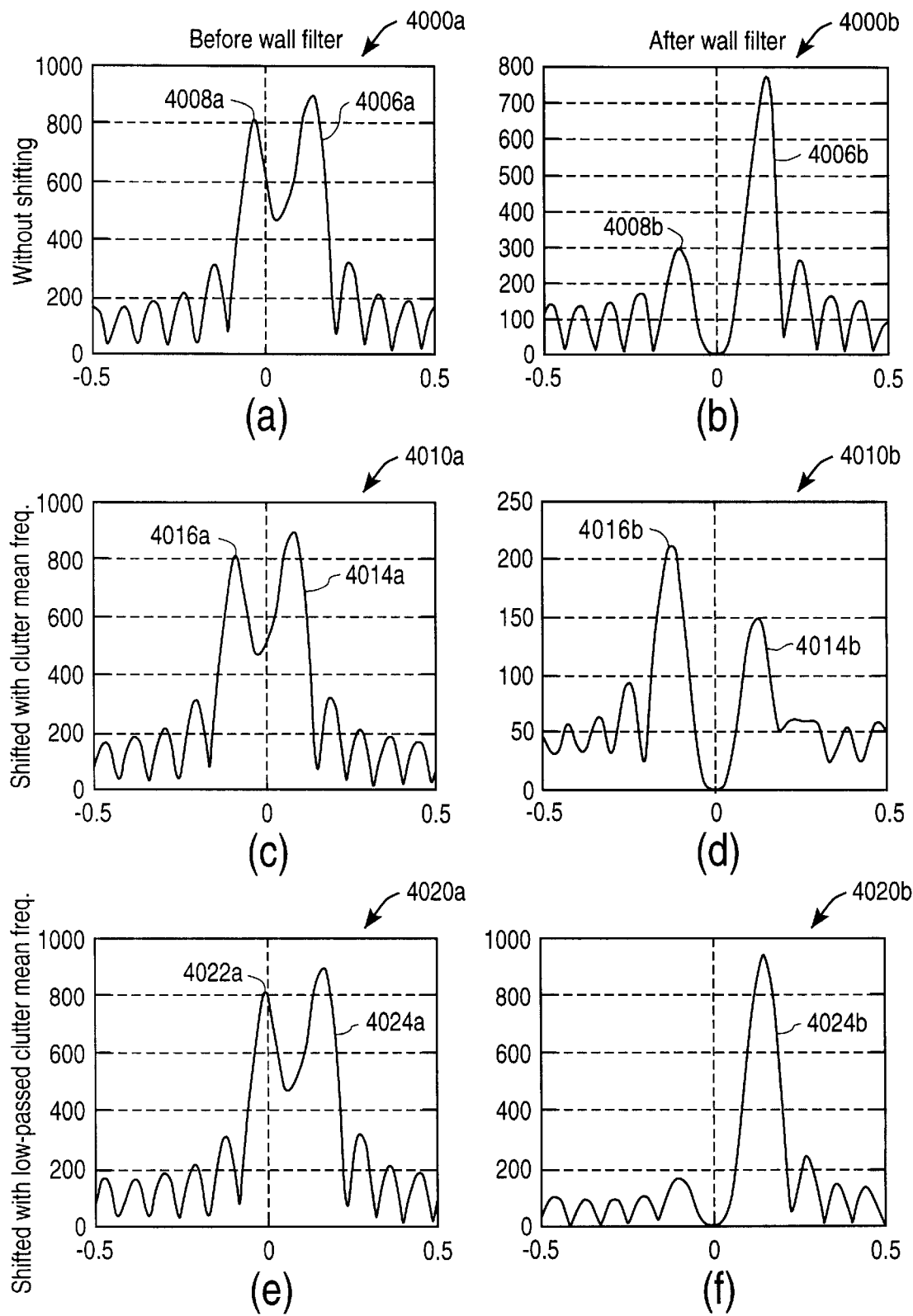
FIG. 4A and FIG. 4B illustrate the input and output of a wall filter in the case in which there has been no shifting.
FIG. 4C and FIG. 4D illustrate the input and output of a wall filter in the case in which there has been spectrum shifting and clutter mean frequency estimation.
FIG. 4E and FIG. 4F illustrate the input and output of a wall filter in the case in which there has been spectrum shifting and low-pass filtering with clutter mean frequency suppression.

FIG. 4 illustrates the inputs and outputs of the wall filter 424 under various test circumstances. In particular, FIG. 4A and 4B illustrate the input and output of wall filter 424 in the case in which there has been no clutter shifting, i.e., there has been no estimate of the clutter mean frequency and attempt to position the clutter at DC. As can be seen in FIG. 4A, the color spectrum 4000a displays a prominent clutter peak 4008a as well as a prominent flow peak 4006a. The clutter peak 4008a is positioned away from DC. FIG. 4B illustrates the spectrum 4000b after it has been high-pass filtered, i.e., at the output of the wall filter 424. The spectrum 4000b thus shows a prominent color flow peak 4006b. The clutter peak 4008a has been generally eliminated, though a residue peak 4000b remains.

FIGS. 4C and 4D show the input and output, respectively, of the wall filter 424 after the clutter spectrum has been shifted and with clutter mean frequency estimation performed thereon. As can be seen in FIG. 4C, the color spectrum 4010a includes a prominent clutter peak 4016a and a flow peak 4014a. In this case, the clutter peak 4016a is actually farther away from DC than in the non-clutter-shifted case.

The output of the wall filter 424 for this case is shown in FIG. 4D. In particular, the wall-filtered spectrum 4010b includes both a prominent clutter peak 4016b and a prominent flow peak 4014b. In this case, however, the magnitude of the clutter peak 4016b is significantly higher than that of the flow peak 4014b. Consequently, any velocity estimates would necessarily show a sub-optimal result. However, as will be seen with regard to FIG. 4E and FIG. 4F, this problem is overcome by the present invention.

More particularly, FIG. 4E and FIG. 4F illustrate the input and output spectra 4020a, 4020b, respectively, of the wall filter 424 in the case in which the color spectrum is low-pass filtered with clutter mean frequency estimation and shifting. As can be seen in FIG. 4E, the clutter peak 4022a of the color spectrum 4020a is positioned almost exactly at DC. The color flow peak 4024a is positioned substantially away from DC. The color spectrum is then high-pass filtered using the wall filter 424 as seen in FIG. 4F. The resulting color spectrum 4020b has a prominent color flow peak 4024b and no clutter peak. Thus, as can be appreciated, the use of the low-pass filter in accordance with the present invention can provide for more accurate clutter removal than standard mean frequency estimation and shifting.

As discussed above, the control processor 421 may be used to dynamically control the low-pass filter bandwidth, depending on test or scan circumstances. For example, a scan of the aorta might require a different filter bandwidth than a scan of the carotid artery. Similarly, a scan at one pulse repetition frequency (PRF) might require a different low-pass filter bandwidth. (The bandwidth of the wall filter may similarly be adjusted). More particularly, the control processor 421 is configured to receive inputs from a sonographer (typically via a keyboard (not shown)), which control scan parameters, such as PRF and the like. A memory 423 coupled to the control processor 421 may include a look-up table defining filter bandwidths for the particular scan. Depending on the input scan parameters, the control processor 421 may access a low-pass filter from the memory 423 for use by the mean frequency estimation unit 422.

Figure 6A:
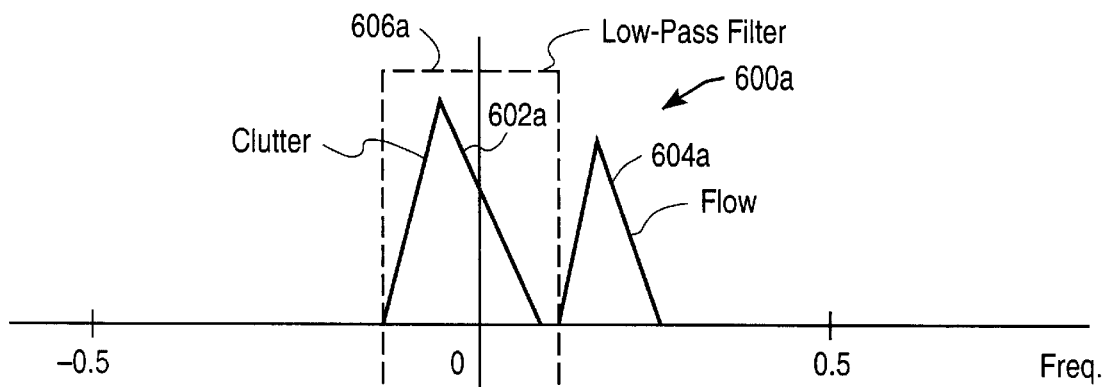
FIGS. 6A, 6B and 6C illustrates exemplary dynamic bandwidth control.
Figure 6B:
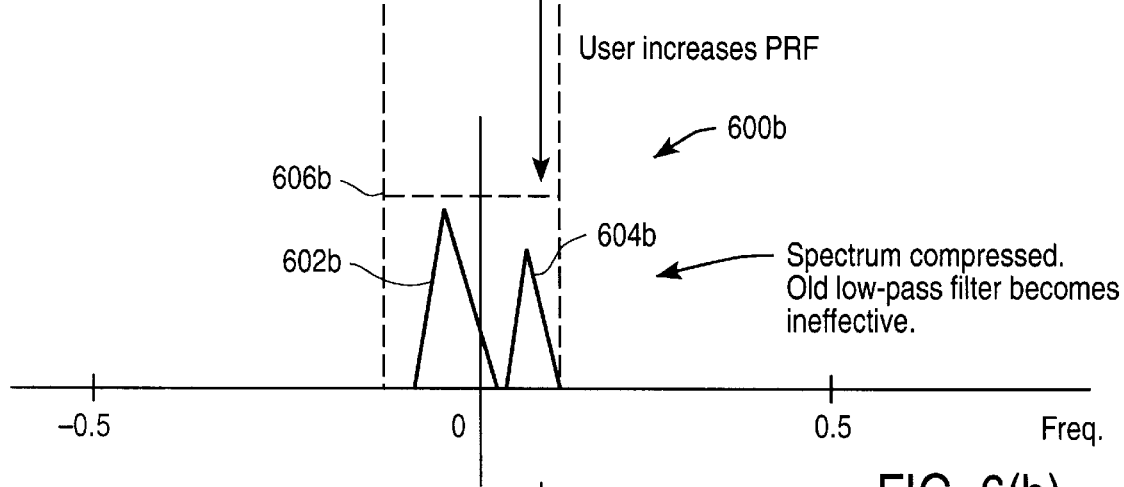
Figure 6C:
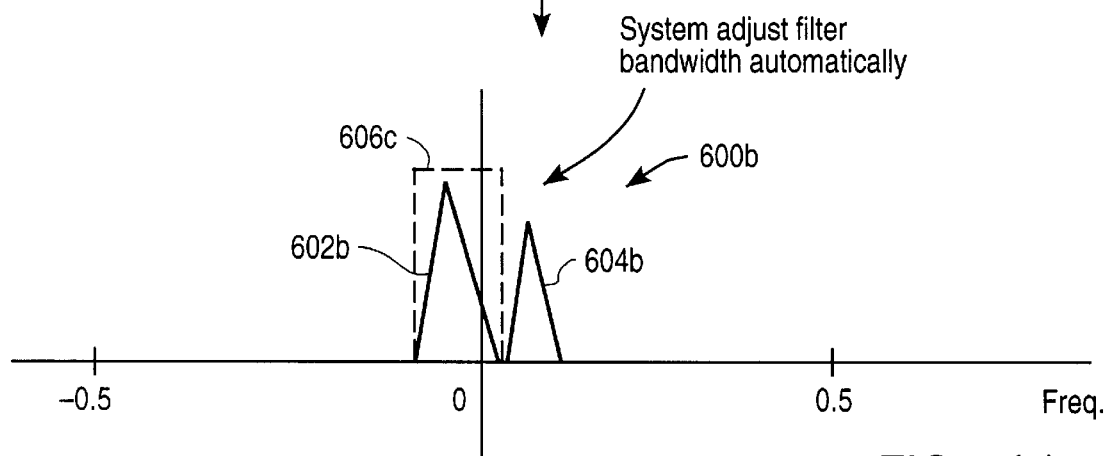

For example, FIG. 6A illustrates a color spectrum 600a having a flow component 604a and a clutter component 602a. A low-pass filter 606a, having exemplary parameters as illustrated by the dashed line, may be used to remove the flow component 604a prior to mean frequency estimation. In FIG. 6B, a color spectrum 600b is shown which represents the case in which the sonographer increases the pulse repetition frequency. The color spectrum 600b has a flow component 604b and a clutter component 602b. If the same filter 606a as used in FIG. 6A is employed, the filter is ineffective to remove the flow component 604b. However, if the bandwidth of the filter is changed, as shown in FIG. 6C, then the flow component may be adequately suppressed.

Finally, it is noted that, while the examples discussed involve shifting to DC, it is possible to perform the clutter filtering without shifting the clutter to DC. However, this is less desirable since a more complex clutter filter is required.

Figure 7:
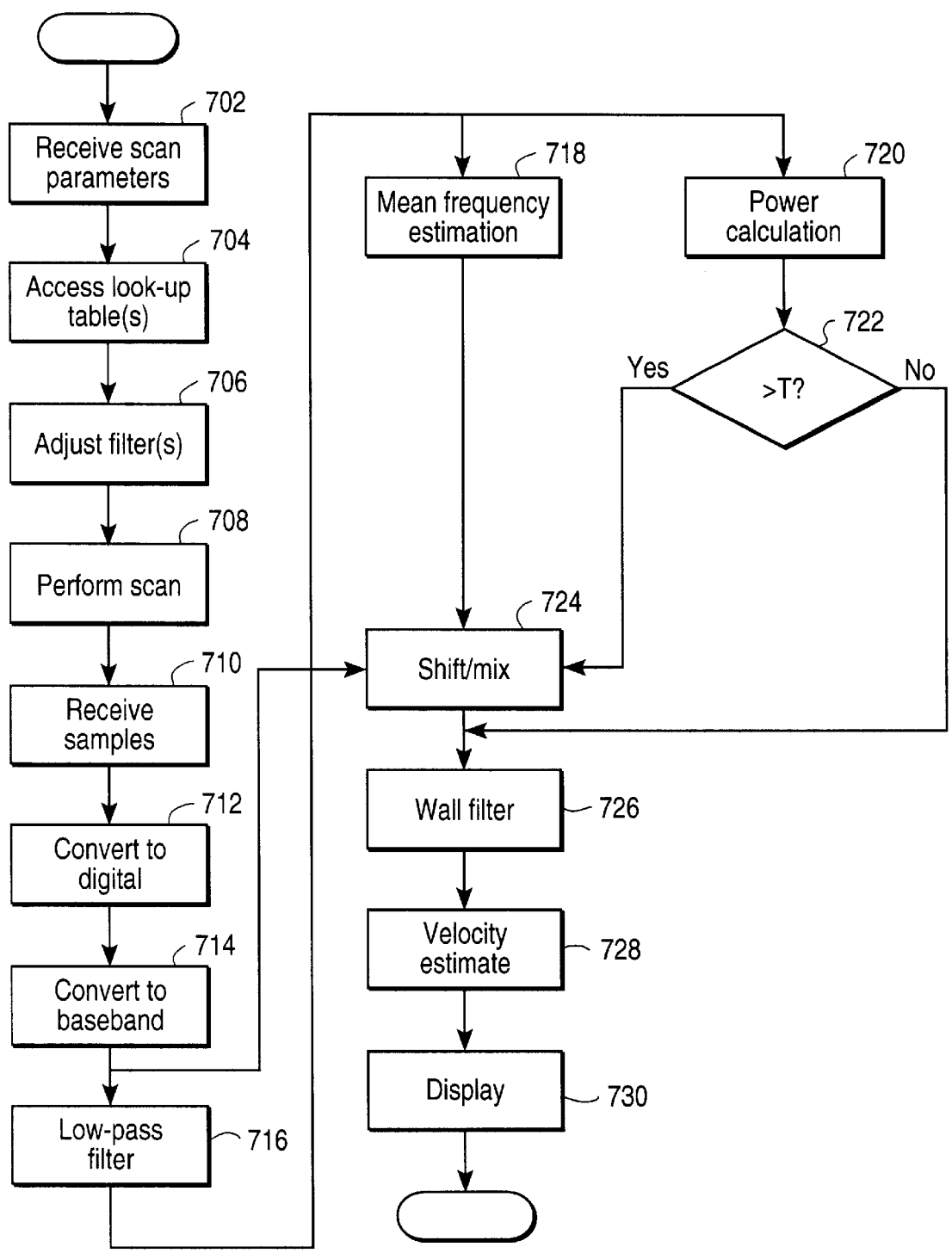
FIG. 7 is a flowchart of operation of an ultrasound system according to an embodiment of the invention.

Turning now to FIG. 7, a flowchart 700 illustrating general operation of an ultrasound system according to an embodiment of the present invention is shown. In particular, in a step 702, the ultrasound system receives scan parameters. The scan parameters are typically received, for example, via keyboard input and processed by the control processor 421. Scan parameters can include, for example, pulse repetition frequencies and other known parameters such as volume to be scanned including the specific target area such as the aorta, carotid artery and the like. in a step 704, the control processor 421 accesses one or more lookup tables in the memory 423. As noted above, the lookup tables may include bandwidth and filter parameters for use by the mean frequency estimation unit 422 and/or the clutter filter 424. In a step 706, the control processor 421 adjusts the filters by instructing the mean frequency estimation unit 422 and/or the clutter filter 424 with the new filter parameters. In a step 708, the sonographer performs the scan on the patient over the designated region. As is well known, the transmitter 410 causes pulses to be emitted from the transducer 412. Received pulses are received at the transducer and the receiver 414 in a step 710. In a step 712, the receiver 414 converts the received signals into digital format. In a step 714, the base band converter 418 converts the received signals down to base band. Next, in a step 716, the low pass filter receives the baseband signal and suppresses the flow component for mean frequency estimation. In a step 718, the mean frequency estimation unit 422 performs a power spectrum calculation on the received, low pass filtered signal. If, in a step 720 the power spectrum magnitude is determined to be less than a predetermined threshold, then in a step 726, the baseband signal bypasses the mean frequency estimation and mixing, and, in a step 726, a wall filtering is performed using the clutter filter 424. Then the velocity estimation unit 726 estimates the velocity in a step 428 and the resulting output is displayed in a step 730.

If, however, in step 722 the power spectrum was greater than a predetermined threshold (such as when clutter is present in significant amounts) then the result of the mean frequency estimation is provided to the mixing unit and, in a step 724, the estimated frequency is mixed with the ultrasound signal to position the clutter frequency at DC. The resulting mixed signal is then provided to the wall filter 424, in a step 726, and the velocity estimation unit 426, in a step 728. The ultrasound signal is then provided to a display in a step 730.

What is claimed is:

1. An ultrasound imaging system, comprising:
   means for receiving an ultrasound signal, said ultrasound signal including a clutter component and a flow component;

means coupled to said receiving means for suppressing said flow component, said suppressing means including a low-pass filter for suppressing said flow component; and means for frequency shifting and mean frequency estimating a resulting low-pass filtered clutter component.

2. The ultrasound imaging system of claim 1, said suppressing means including a means for high-pass filtering said ultrasound signal after said mean frequency estimation and frequency shift.

3. The ultrasound imaging system of claim 1, wherein said low-pass filter is a regression-type filter.

4. The ultrasound imaging system of claim 1, wherein said low-pass filter is an analog filter.

5. A method for processing ultrasound signals, comprising:

receiving an ultrasound signal including a flow component and a clutter component;

filtering said ultrasound signal to remove said flow component during a frequency estimation;

using an output of said frequency estimation to position said ultrasound signal such that said clutter component is substantially at a predetermined frequency; and filtering said ultrasound signal to remove said clutter component at said predetermined frequency.

6. A method according to claim 5, wherein said filtering to remove said flow component is digital low-pass filtering.

7. A method according to claim 5, wherein said filtering to remove said flow component is analog low-pass filtering.

8. A method according to claim 6, wherein said digital low-pass filtering is regression filtering.

9. An ultrasound imaging system, comprising:

one or more transducers for transmitting ultrasound energy into a target region of a patient;

a receiver configured to receive reflected ultrasound energy and providing a received ultrasound signal, said received ultrasound signal including a clutter component and a flow component; and a clutter suppression system, said clutter suppression system including:

a first filter for suppressing said flow component from said ultrasound signal;

a frequency estimator, responsive to said ultrasound signal having said flow component suppressed, for determining a frequency estimate of said clutter component; and a second filter for removing said clutter component from said ultrasound signal after said frequency estimate of said clutter component has been made.

10. An ultrasound system according to claim 9, wherein said first filter is a low-pass regression filter.

11. An ultrasound system according to claim 9, wherein said second filter is a high-pass filter.

12. An ultrasound system according to claim 1, further including means for dynamically changing a bandwidth of said low-pass filter depending on scan parameters.

13. An ultrasound system according to claim 12, further including means for dynamically changing a bandwidth of said high-pass filter depending on said scan parameters.

14. An ultrasound system according to claim 1, wherein said suppressing means includes means for bypassing said frequency shift of a power spectrum of said clutter component is less than a predetermined threshold.

* * * * *